United States Patent [19]
Lerch et al.

[11] 3,991,188
[45] Nov. 9, 1976

[54] 3-ALKYL-4-SULFAMOYL-ANILINE THERAPEUTIC COMPOSITIONS

[75] Inventors: Ansgar Lerch, Kirrlach; Alfred Popelak, Rimbach; Kurt Stach, Mannheim-Waldhof; Egon Roesch, Lampertheim; Klaus Hardebeck, Ludwigshafen (Rhine), all of Germany

[73] Assignee: Boehringer Mannheim G.m.b.H., Mannheim, Waldhof, Germany

[22] Filed: July 3, 1975

[21] Appl. No.: 593,089

Related U.S. Application Data

[62] Division of Ser. No. 371,212, June 18, 1973, Pat. No. 3,914,219.

[30] Foreign Application Priority Data

July 1, 1972 Germany............................ 2232457

[52] U.S. Cl................................. 424/228; 424/229
[51] Int. Cl.²................ A61K 31/63; A61K 31/625
[58] Field of Search.................. 260/239.6; 424/229, 424/228

[56] References Cited
UNITED STATES PATENTS 2,910,488   10/1959   Novello............................ 260/397.7
3,565,920   2/1971    Werner............................ 260/347.2
3,665,002   5/1972    Popelak et al..................... 260/239.9

*Primary Examiner*—Stanley J. Friedman
*Attorney, Agent, or Firm*—Burgess, Dinklage & Sprung

[57] ABSTRACT

New 3-alkyl-4-sulfamoyl-aniline compounds of the formula

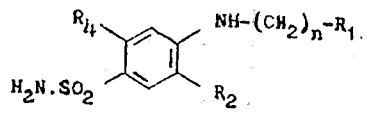

wherein
  $R_1$ is phenyl, furyl or thienyl;
  $R_2$ is carboxyl or tetrazolyl-(5)
  $R_4$ is a straight-chain or branched alkyl radical of from 2 to 5 carbon atoms; and
  $n$ is 1 or 2;

and the pharmacologically compatible salts thereof; are outstandingly effective saluretic compounds, particularly when administered enterally.

19 Claims, No Drawings

3-ALKYL-4-SULFAMOYL-ANILINE THERAPEUTIC COMPOSITIONS

This is a division of application Ser. No. 371,212, filed June 18, 1973, now U.S. Pat. No. 3,914,219.

The present invention is concerned with new 3-alkyl-4-sulfamoyl-aniline compounds and with therapeutic compositions containing them.

The new 3-alkyl-4-sulfamoyl-aniline derivatives according to the present invention are compounds of the formula:

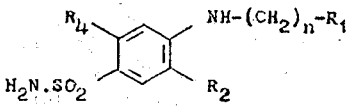
(I)

wherein
$R_1$ is phenyl, furyl or thienyl;
$R_2$ is carboxyl or tetrazolyl-(5)
$R_4$ is a straight-chain or branched alkyl radical of from 2 to 5 carbon atoms; and
$n$ is 1 or 2;
and the pharmacologically compatible salts thereof.

In German Pat. No. 2,034,986, there are described 4-sulfamoyl-m-toluidine derivatives of general formula (I) in which $R_4$ is a methyl radical. These compounds possess diuretic and saluretic properties.

We have now found that by replacement of the methyl radical by a higher alkyl radical, very good saluretic compounds are obtained, some of which are substantially more effective than the known compounds when administered enterally.

The new compounds according to the present invention can be prepared, for example by one of the following methods a. reaction of a compound of the general formula:

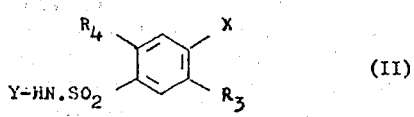
(II)

wherein $R_3$ has the same meaning given above for $R_2$ or is a group which can be converted into $R_2$, $R_4$ has the same meaning as above, Y is a hydrogen atom or an acyl radical and X is a halogen atom or a nitro group, with an amine of the general formula:

$$H_2N-(CH_2)_n-R_1 \qquad (III)$$

wherein $R_1$ and $n$ have the same meanings as above; or b. reaction of a compound of the general formula

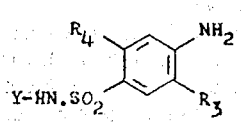
(IV)

wherein $R_3$, $R_4$ and Y have the same meanings as above, with a compound of the general formula:

$$Z-(CH_2)_n-R_1 \qquad (V)$$

wherein $R_1$ and $n$ have the same meanings as above and Z is a reactive ester group, or with a compound of the general formula:

$$OHC-(CH_2)_m-R_1 \qquad (VI)$$

wherein $R_1$ has the same meaning as above and $m$ is 0 or 1, and optionally hydrogenates simultaneously or subsequently, when $R_3$ is a group which can be converted into a carboxyl group or into a tetrazolyl-(5) radical, this is converted into the substituent $R_2$ and, when Y is an acyl radical, this is split off in known manner, whereupon the compound obtained is, if desired, converted into a pharmacologically compatible salt.

Substituents which can be converted into a carboxyl group include, for example, esterified carboxyl groups and carboxamido and nitrile groups, as well as carboxyl groups in the form of salts with inorganic and organic bases. Preferred groups which can be converted into the tetrazolyl-(5) radical include nitrile, imido ester and amidine groups.

Compounds V with a reactive ester group Z include halides, the quaternary addition compound thereof, for example with pyridine, and sulfonic acid esters which can easily be split off, for example tosylates and brosylates.

The starting materials of general formula (II) are advantageously obtained by the sulfochlorination of, for example, 4-alkyl-2-bromobenzoic acids or of their derivatives, with chlorosulfonic acid and subsequent reaction with ammonia.

The starting materials of general formula (IV) can be obtained, for example, by sulfoamidation of 4-alkyl-2-nitrobenzoic acids or of their derivatives and subsequent reduction. The corresponding tetrazolyl compounds can be prepared by the reduction of the nitriles with azides.

The process according to the present invention can be carried out at a temperature between 60° and 180° C., advantageously with the use of an excess of the basic reaction component simultaneously serving to take up the acid liberated by the reaction. For this purpose, there can, however, also be used other inorganic or organic bases or basically reacting compounds as examples thereof, mention may be made of alkali metal carbonates, calcium oxide, triethylamine, dimethyl-aniline and pyridine. The reaction can be carried out with or without the use of an inert solvent or diluent, aromatic hydrocarbons, ethylene glycol, ethylene glycol monomethyl ether, diethylene glycol dimethyl ether, dimethyl formamide and dimethyl sulfoxide having proved to be useful for this purpose. In the case of reactions using inexpensive halides of general formula (V), these can themselves be used as solvents.

The reaction of the primary amines of general formula (IV) with carbonyl compounds of general formula (VI) gives the corresponding Schiff bases which are subsequently reduced in known manner either catalytically in an inert solvent or with reducing agents, for example, sodium boro-hydride.

When $R_3$ is an esterified carboxyl group or a carboxamido or nitrile group, these can subsequently be converted into a carboxyl group by hydrolysis, preferably in an alkaline medium.

When it is desired to obtain compounds of general formula (I) in which $R_2$ is a tetrazolyl-(5) group, the corresponding compounds in which $R_3$ is a nitrile, imido ester or amidine group can be reacted with hydrazoic acid or, preferably, with a salt thereof. The reaction can be carried out in an inert solvent, preferably in dimethyl formamide.

The splitting off of an acyl radical Y can be carried out by alkaline saponification, preferably with an aqueous solution of an alkali metal hydroxide.

The crude products of general formula (I) can be purified by dissolving in an aqueous solution of an alkali metal hydroxide and subsequent precipitating them again with a dilute mineral acid.

If desired, the products obtained can be converted into the corresponding salts by reaction with inorganic or organic bases. Preferred physiologically compatible salts include the alkali metal, alkaline earth metal and ammonium salts, which can be prepared, for example, by reaction with an aqueous solution of sodium hydroxide, potassium hydroxide, ammonia or a corresponding carbonate.

The following Examples are given for the purpose of illustrating the preparation of the compounds of the present invention:

EXAMPLE 1

Preparation of 4-Ethyl-2-furfurylamino-5-sulfamoylbenzoic acid.

10 g. 4-ethyl-2-bromo-5-sulfamoylbenzoic acid were heated for 12 hours at 140° C. with 30 ml. furfurylamine. After cooling, the reaction mixture was mixed with 100 ml. 2N aqueous sodium hydroxide solution and then extracted with ether. The aqueous phase was treated with active charcoal, filtered and the filtrate was acidified with hydrochloric acid. The crude product which separates out in crystalline form, was filtered off with suction and recrystallized from dilute ethanol. There were obtained 6.5 g. (62% of theory) 4-ethyl-2-furfurylamino-5-sulfamoylbenzoic acid in the form of colorless crystals which melted at 228° C.

The following compounds were prepared in an analogous manner:

4-ethyl-2-thenylamino-5-sulfamoylbenzoic acid from 4-ethyl-2-bromo-5-sulfamoylbenzoic acid and thenylamine; yield 68% of theory; m.p. 227°–228° C., after recrystallization from ethanol;

For the preparation of the sodium salt, 2 g. of the product were dissolved, with warming, in 5 ml. 2N aqueous sodium carbonate solution. Upon cooling, the sodium salt crystallizes out. It has a melting point of 277° C.

3-ethyl-4-sulfamoyl-6-tetrazolyl-(5)-N-furfurylaniline from 3-ethyl-4-sulfamoyl-6-tetrazolyl-(5)-1-bromobenzene and furfurylamine; yield 65% of theory; m.p. 179°–180° C., after recrystallization from ethanol;

3-ethyl-4-sulfamoyl-6-tetrazolyl-(5)-N-benzylaniline frm 3-ethyl-4-sulfamoyl-6-tetrazolyl-(5)-1-bromobenzene and benzylamine; yield 71% of theory; m.p. 237°–239° C., after recrystallization from acetone/ethanol;

4-isopropyl-2-benzylamino-5-sulfamoylbenzoic acid from 4-isopropyl-2-bromo-5-sulfamoylbenzoic acid and benzylamine; yield 59% of theory; m.p. 233°–234° C., after recrystallization from methanol/water;

4-isopropyl-2-furfurylamino-5-sulfamoylbenzoic acid from 4-isopropyl-2-bromo-5-sulfamoylbenzoic acid and furfurylamine; yield 54% of theory; m.p. 180°–182° C. (decomp.), after recrystallization from methanol/water;

4-isopropyl-2-thenylamino-5-sulfamoylbenzoic acid from 4-isopropyl-2-bromo-5-sulfamoylbenzoic acid and thenylamine; yield 56% of theory; m.p. 194°–197° C. (decomp.), after recrystallization from methanol/water;

4-butyl-2-furfurylamino-5-sulfamoylbenzoic acid from 4-butyl-2-bromo-5-sulfamoylbenzoic acid and furfurylamine; yield 72% of theory; m.p. 239°–240° C., after recrystallization from acetone/ethanol;

4-butyl-2-(2-furylethylamino)-5-sulfamoylbenzoic acid from 4-butyl2-bromo-5-sulfamoylbenzoic acid and 2-furylethylamine; yield 72% of theory; m.p. 227°–228° C., after recrystallization from acetone/ethanol;

4-butyl-2-thenylamino-5-sulfamoylbenzoic acid from 4-butyl-2-bromo-5-sulfamoylbenzoic acid and thenylamine; yield 64% of theory; m.p. 229°–230° C., after recrystallization from acetone/ethanol;

3-ethyl-4-sulfamoyl-6-tetrazolyl-(5)-N-thenylaniline from 3-ethyl-4-sulfamoyl-6-tetrazolyl-(5)-1-bromobenzene and thenylamine; yield 79% of theory; m.p. 196°–198° C., after recrystallization from ethanol/water;

3-isopropyl-4-sulfamoyl-6-tetrazolyl-(5)-N-thenylaniline from 3-isopropyl-4-sulfamoyl-6-tetrazolyl-(5)-1-bromobenzene and thenylamine; yield 52% of theory; m.p. 194°–195° C. (decomp.), after recrystallization from ethyl acetate.

The starting materials used can be prepared according to the following general methods:

a. 4-alkyl-2-bromobenzonitrile

1 Mole 4-alkyl-2-bromo-aniline was diazotized with sodium nitrate at 0°–5° C. in a solution of sulfuric acid. The clear, ice-cooled diazonium salt solution was then added dropwise to a solution of copper cyanide at 60° C., this solution having been prepared from 1.5 mole crystalline copper sulfate and 6 mole sodium cyanide. The reaction mixture was stirred for 2 hours at 60° C., and thereafter left to stand overnight. The brown precipitate was then filtered off with suction and immediately subjected to steam distillation. The distillate was extracted with methylene chloride and the combined methylene chloride extracts were then washed with a 1N aqueous sodium hydroxide solution and finally with water and then dried. The residue remaining after removal of the solvent is fractionally distilled in a vacuum. The compounds set out in the following Table I can be prepared in this manner:

TABLE I

| alkyl radical | boiling point |
|---|---|
| $C_2H_5$ | 106 – 110° C./1 mm.Hg. |
|  | 115 – 117° C./3 mm.Hg. |
| iso-$C_3H_7$ | 95 – 100° C./0.2 mm.Hg. |
|  | 110 – 115° C./0.5 mm.Hg. |
| n-$C_4H_9$ | 110 – 112° C./0.05 mm.Hg. |
|  | 140 – 144° C./3.5 mm.Hg. | b. 4-alkyl-2-bromobenzoic acid 50 g. 4-alkyl-2-bromobenzonitrile were heated with a mixture of 130 ml. concentrated sulfuric acid and 40 ml. water for 1 hour at 130° C. Thereafter, a further 100 ml. water were added thereto and the reaction mixture was heated for 2 hours at 160° C. After leaving to cool the reaction mixture was poured into ice water and the precipitate obtained was filtered off with suction. The still moist material obtained as dissolved in 300 ml. 2N aqueous sodium hydroxide solution, extracted with methylene chloride and the aqueous phase was treated with animal charcoal and then acidified with hydrochloric acid. The product obtained was filtered off with suction, washed with water and dried. The compounds set out in the following Table II can be prepared in this manner:

TABLE II

| alkyl radical | melting point |
|---|---|
| $C_2H_5$ | 89 – 91° C. (recrystallised from ligroin) |
| iso-$C_3H_7$ | 70 – 72° C. |
| n-$C_4H_9$ | 73° C. (recrystallised from ligroin) | c. 4-alkyl-2-bromo-5-sulfamoylbenzoic acid 50 g. 4-alkyl-2-bromobenzoic acid, together with 150 ml. chlorosulfonic acid, were heated for 2 hours at 100° C. After cooling, the reaction mixture was poured on to ice and the precipitated sulfochloride was filtered off with suction. The still moist material was introduced at 20° C. into 500 ml. concentrated aqueous ammonium hydroxide solution and left to stand overnight. The clear solution was then treated with active charcoal, filtered and the filtrate concentrated somewhat in a vacuum in order to remove the main amount of ammonia. The concentrate was now acidified with hydrochloric acid and the precipitated crude product was filtered off with suction and then recrystallized from dilute alcohol. The compounds set out in the following Table III can be prepared in this manner:

TABLE III

| alkyl radical | melting point |
|---|---|
| $C_2H_5$ | 215 – 216° C. |
| iso-$C_3H_7$ | 216 – 218° C. |
| n-$C_4H_9$ | 210 – 211° C. | d. 3-alkyl-6-tetrazolyl-(5)-bromobenzene 0.1 mole 4-alkyl-2-bromobenzonitrile was dissolved in 200 ml. dimethyl formamide, 20 ml. water, 0.12 mole sodium azide and 0.12 mole ammonium chloride were added thereto and the reaction mixture was then heated, while stirring, for 15 hours at 100° C. Subsequently, the solvent was distilled off in a vacuum and the residue was taken up in 1N aqueous sodium hydroxide solution. This solution was extracted with methylene chloride, treated with charcoal, filtered and the filtrate acidified with glacial acetic acid. The precipitated crude product was filtered off with suction and dried. The compounds set out in the following Table IV can be prepared in this manner:

TABLE IV

| alkyl radical | melting point |
|---|---|
| $C_2H_5$ | 142 – 144° C. (recrystallised from ethanol) |
| iso-$C_3H_7$ | 101 – 105° C. | e. 3-alkyl-4-sulfamoyl-6-tetrazolyl-(5)-bromobenzene

3-Alkyl-6-tetrazolyl-(5)-bromobenzene was sulfochlorinated with the twofold amount by weight of chlorosulfonic acid. When the reaction was finished, the reaction mixture was poured on to ice and the precipitated sulfochloride was filtered off with suction. While still moist, this was introduced at 20° C. into a concentrated aqueous solution of ammonium hydroxide and left to stand overnight. The clear solution was treated with active charcoal, filtered and the filtrate concentrated somewhat in a vacuum. The concentrated was then acidified with hydrochloric acid and the crude product obtained was filtered off with suction and then recrystallized from methanol/water. The compounds set out in the following Table V can be prepared in this manner:

TABLE V

| alkyl radical | reaction temp. | reaction time | m.p. |
|---|---|---|---|
| $C_2H_5$ | 150° C. | 2 hrs. | 235 – 236° C. |
| iso-$C_3H_7$ | 100° C. | 17 hrs. | 195 – 196° C. |

For use as pharmaceuticals with a diuretic and natriuretic action, the new compounds according to the present invention can, in principle, be used in all the conventional enteral and parenteral forms of administration. For this purpose, the active materials were mixed with solid or liquid pharmaceutical diluents or carriers and then brought into a suitable form.

Examples of solid carrier materials include lactose, mannitol, starch, talc, methyl cellulose, gelatine and the like, to which, if desired, can be added coloring materials and/or flavorings. Because of the low solubility of the compounds according to the present invention, for injectable solutions very few solvents can be used, for example dimethyl sulfoxide. Higher concentrations are, therefore, preferably administered in the form of suspensions. In human medicine, in the case of enteral administration, doses of active materials of between 10 and 500 mg. per day in 1 to 4 individual doses have proved to be useful; in the case of intravenous administration, the most favorable dosage range is between 5 and 100 mg. per day.

The new compounds according to the present invention have a strong, rapidly commencing diuretic action. Simultaneously with the increased excretion of water, an increased amount of sodiums is also excreted. The increased excretion of potassium ions, which occurs simultaneously in the case of comparable known substances, is, in the case of the compounds according to the present invention, considerably lower. In this way, higher sodium-potassium quotients are obtained, i.e., the new compounds according to the present invention enable the physician to bring about in his patients a rapid, sudden and considerably increased excretion of water and of sodium ions without, at the same time, substantially influencing the potassium balance.

The compounds of this invention possess outstanding saluretic properties as well. In order to establish the effectiveness of compounds representative of this invention as therapeutic agents for diuretic and saluretic purposes, the following series of tests were carried out.

The test animals were female Sprague-Dawley rats each weighing between 140–200 grams. The rats were kept in climate-controlled rooms at 23 ± 1° C and a relative humidity of 60 ± 5% for at least 1 week prior to the tests. On the evening prior to the test day (i.e., 16 hours prior to administration of test compounds), the test rats were left without food and had access only to drinking water. During the tests, groups of animals were placed into metabolic cages and such groups of animals were used in the tests. The test compounds were administered to the test animals as a suspension in 5% tylose at the rate of 10 milliliters per kg of body weight of each rat. The test preparations were injected intraperitoneally or administered orally. The dosage in terms of milligrams of test compounds per kg of body weight is set forth in the Table below. Prior to the test and after 2 hours and again after 6 hours subsequent to the test, the bladders of the rats were emptied by squeezing, the urine content was measured, sodium and potassium were determined by flame photometric tests.

The following were the test compounds: (The numbered compounds below are representative of the invention; the lettered compounds, i.e., compounds A, B, C and D are the 3-methyl analogs of the representative compounds of the instant invention and are included for purposes of comparison.)

| Compound No. | |
|---|---|
| A | 4-Sulfamoyl-6-carboxy-N-thenyl-m-toluidine |
| 1 | 4-Ethyl-2-thenylamino-5-sulfamoyl-benzoic acid |
| B | 4-Sulfamoyl-6-tetrazolyl(5)-N-benzyl-m-toluidine |
| 2 | 3-Ethyl-4-sulfamoyl-6-tetrazolyl(5)-N-benzylaniline |
| C | 4-Sulfamoyl-6-carboxy-N-benzyl-m-toluidine |
| 3 | 4-Isopropyl-2-benzylamino-5-sulfamoylbenzoic acid |
| D | 4-Sulfamoyl-6-tetrazolyl(5)-N-thenyl-m-toluidine |
| 4 | 3-Isopropyl-4-sulfamoyl-6-tetrazolyl(5)-N-thenylaniline |
| 5 | 4-Isopropyl-2-thenylamino 5-sulfamoyl benzoic acid |

The comparison compounds are disclosed in U.S. application Ser. No. 156,481, filed June 24, 1971, and now abandoned.

The results are set forth in the Table below.

| | | Diuretic and Saluretic Properties of Illustrating Compounds Relative to 3-Methyl Counterparts Thereof (Urea and Salt Excretion in Rats) | | | | | | | |
|---|---|---|---|---|---|---|---|---|---|
| | | | | | Separation/kg During | | | | |
| | Dosage | Two Hours | | | Na | Six Hours | | | Na |
| Test Compound | mg/kg | ml urine | Na | K | K | ml urine | Na | K | K |
| Control i.p. | i.p. | 6 | 0.05 | 0.22 | 0.3 | 9 | 0.17 | 0.56 | 0.3 |
| A | 50 | 47 | 4.7 | 1.1 | 4.1 | 53 | 5.0 | 1.9 | 2.7 |
| 1 | 50 | 36 | 4.5 | 0.84 | 5.3 | 40 | 4.7 | 1.3 | 3.5 |
| B | 50 | 43 | 4.6 | 1.2 | 3.8 | 54 | 5.4 | 2.0 | 2.8 |
| 2 | 50 | 42 | 4.9 | 0.90 | 5.5 | 52 | 5.9 | 1.7 | 3.4 |
| C | 50 | 38 | 4.4 | 1.1 | 4.1 | 42 | 4.5 | 1.6 | 2.8 |
| 3 | 50 | 29 | 3.3 | 0.56 | 5.9 | 30 | 3.4 | 0.82 | 4.1 |
| Control p.o. | p.o. | 9 | 0.10 | 0.22 | 0.5 | 13 | 0.43 | 0.62 | 0.7 |
| D | 25 | 10 | 0.28 | 0.20 | 1.4 | 25 | 2.1 | 1.0 | 2.1 |
| 4 | 25 | 9 | 0.19 | 0.25 | 0.7 | 34 | 2.8 | 1.2 | 2.2 |
| A | 50 | 24 | 1.4 | 0.75 | 1.9 | 35 | 2.7 | 1.5 | 1.8 |
| 5 | 50 | 41 | 3.4 | 0.97 | 3.6 | 43 | 3.6 | 1.3 | 2.6 |

It will be understood that the specification and examples are illustrative but not limitative of the present invention and that other embodiments within the spirit and scope of the invention will suggest themselves to those skilled in the art.

What is claimed is:

1. A therapeutic composition having diuretic and saluretic activity comprising a pharmacologically acceptable carrier and, in effective amount, a sulfamoylaniline compound of the formula:

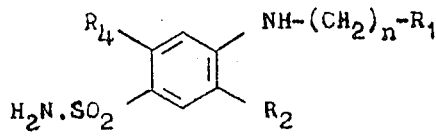

wherein
R$_1$ is phenyl, furyl or thienyl;
R$_2$ is carboxyl or tetrazoyl-(5)
R$_4$ is a straight-chain or branched alkyl radical of from 2 to 5 carbon atoms;
n is 1 or 2;
or a pharmacologically compatible salt thereof.

2. Method of treating an afflicted subject to stimulate excretion, which method comprises administering to such subject an effective amount of a 3-alkyl-4-sulfamoyl compound of the formula:

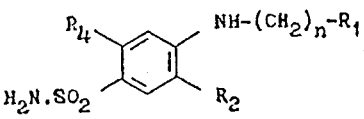

wherein
R$_1$ is phenyl, furyl or thienyl;
R$_2$ is carboxyl or tetrazoyl-(5)
R$_4$ is a straight-chain or branched alkyl radical of from 2 to 5 carbon atoms; and
n is 1 or 2;
or a pharmacologically compatible salt thereof.

3. Method as claimed in claim 2, wherein said compound is administered enterally.

4. Method as claimed in claim 2, wherein said compound is administered at a dosage of from 5 to 100 mg per day per 50 kg of bodyweight of the subject.

5. Method as claimed in claim 2, wherein said compound is
4-ethyl-2-thenylamino-5-sulfamoylbenzoic acid
3-ethyl-4-sulfamoyl-6-tetrazolyl(5)-N-benzylaniline
4-isopropyl-2-benzylamino-5-sulfamoylbenzoic acid
4-isopropyl-2-thenylamino-5-sulfamoyl benzoic acid
or
3-isopropyl-4-sulfamoyl-6-tetrazolyl(5)-N-thenylaniline.

6. Therapeutic composition as claimed in claim 1 wherein R$_1$ in the formula is phenyl.

7. Therapeutic composition as claimed in claim 1 wherein R$_1$ in the formula is furyl.

8. Therapeutic composition as claimed in claim 1 wherein R$_1$ in the formula is thienyl.

9. Therapeutic composition as claimed in claim 1 wherein R$_2$ in the formula is carboxyl.

10. Therapeutic composition as claimed in claim 1 wherein R$_2$ of the formula is tetrazolyl-(5).

11. Therapeutic composition as claimed in claim 1 wherein $R_4$ in the formula is ethyl.

12. Therapeutic composition as claimed in claim 1 wherein $R_4$ in the formula is propyl.

13. Therapeutic composition as claimed in claim 1 wherein $R_4$ in the formula is butyl.

14. Therapeutic composition as claimed in claim 1 wherein $R_4$ is pentyl.

15. Therapeutic composition as claimed in claim 1 wherein said compound is 4-ethyl-2-thenylamino-5-sulfamoylbenzoic acid.

16. Therapeutic composition as claimed in claim 1 wherein said compound is 3-ethyl-4-sulfamoyl-6-tetrazolyl-(5)-N-benzylaniline.

17. Therapeutic composition as claimed in claim 1 wherein said compound is 4-isopropyl-2-benzylamino-5-sulfamoyl-benzoic acid.

18. Therapeutic composition as claimed in claim 1 wherein said compound is 4-isopropyl-2-thenylamino-5-sulfamoyl-benzoic acid.

19. Therapeutic composition as claimed in claim 1 wherein said compound is 3-isopropyl-4-sulfamoyl-6-tetrazolyl-(5)-N-thenylaniline.

* * * * *